United States Patent [19]

Halcomb et al.

[11] Patent Number: 5,104,982
[45] Date of Patent: Apr. 14, 1992

[54] ROUTE TO GLYCALS IN THE ALLAL AND GULAL SERIES

[75] Inventors: Randall L. Halcomb; Samuel J. Danishefsky, both of New Haven; Mark D. Wittman, Hamden, all of Conn.

[73] Assignee: Yale University, New Haven, Conn.

[21] Appl. No.: 498,262

[22] Filed: Mar. 23, 1990

[51] Int. Cl.$^5$ ............................................ C07H 11/02
[52] U.S. Cl. .................................. 536/18.7; 536/124; 536/4.1; 536/18.2; 549/377
[58] Field of Search ..................... 536/124, 4.1, 18.7, 536/124, 4.1, 18.7; 549/377

[56] References Cited

U.S. PATENT DOCUMENTS 4,935,503  6/1990  Naicker et al. .................... 536/18.7

OTHER PUBLICATIONS

Advances in Carbohydrate Chem & Biochem vol. 24, (1969) (Ferrier et al) pp. 199-266.

*Primary Examiner*—Ronald W. Griffin
*Assistant Examiner*—Louise Leary
*Attorney, Agent, or Firm*—Dressler, Goldsmith, Shore, Sutker & Milnamow, Ltd.

[57] ABSTRACT

Axial anomeric sulfoxides generated via thiophenol Ferrier rearrangement of glucal and galactal derivatives are used to synthesize glycals of the gulal and allal series. An application of the method led to the synthesis of the esperamicin thiosugar.

6 Claims, 7 Drawing Sheets

ROUTE TO GLYCALS IN THE ALLAL AND GULAL SERIES

TECHNICAL FIELD

The present invention relates to substituted glycal compounds, and more particularly to a method of preparing a substituted glycal compound having a 3-axial-hydroxyl group or derivative thereof from a similarly substituted glycal having a 3-equatorial-O-ester group.

BACKGROUND

Naturally-occurring DNA intercalating antibiotics are complex molecules that typically contain a multi-ring aglycone portion such as an anthracycline that is linked to one or more glycosides that themselves can be linked to one or more additional glycosidic rings or other structures. Exemplary of such antibiotics are daunorubicin (daunomycin), doxorubicin, (adriamycin), the bleomycins, plicamycin (mithramycin), the esperamicins and the calicheamicins.

Oligosaccharide-containing antibiotics also exist that further contain a single aromatic ring compound. One such antibiotic is lasacoid A, which forms lipid soluble complexes with divalent calcium ions as well as with essential amines such as catecholamines.

The glycoside-containing portion of such molecules is typically a substituted oligosaccharide. The oligosaccharide often itself contains relatively unusual sugar components such as daunosamine in the case of daunorubicin and doxorubicin, and L-gulose and 3-O-carbamoyl-D-mannose for the bleomycins.

The oligosaccharide portions of the esperamicins and the calicheamicins are still more complex, with both molecules containing four glycosidic units and a substituted benzene moiety. The glycosidic units of both esperamicins and calicheamicins include one sulfur substituent-containing glycoside unit, one N-ethylamine substituent-containing glycoside unit and one glycoside unit that contains a glycosidic bond formed by linkage through the oxygen atom of a hydroxylamine substituent group whose nitrogen atom is bonded to the ring of the sulfur substituent-containing glycoside.

Laboratory syntheses of antibiotics such as those discussed before can be carried out by separate formation of the multiring or single ring aglycone and oligosaccharide portions of the molecules, followed by linking of the two portions to form the complete antibiotic, or by adding glycoside units one or more at a time to the multiring aglycone portion and then to each other. Such syntheses are usually arduous not only because the aglycone components are often difficult to prepare, but also because the oligosaccharide portions are also difficultly made, typically containing relatively unusual glycosidic units, and because each glycosidic linkage must be formed stereospecifically.

Thus, for the oligosaccharide portions, contrary to the recent advances in the step-wise syntheses of polypeptides and oligonucleotides, there have heretofore neither been techniques nor reagents available whereby the synthetic chemist could readily prepare a desired oligosaccharide in a relatively routine manner. Recent advances in the step-wise syntheses of oligosaccharide and other poly- or oligoglycosidic molecules have been reported by Danishefsky and co-workers [(a) Halcomb et al., *J. Am. Chem. Soc.*, 111:6661 (1989); and (b) Friesen et al., *J. Am. Chem. Soc.*, 111:6656 (1989)] who reported that a number of glycosidic units could be linked in a step-wise manner not dissimilar to a step-wise polypeptide synthesis to prepare glycosidic compounds having predetermined, stereo-controlled glycosidic linkages.

Those reported advances utilized substituted glycal compounds as key intermediates in the stereo-controlled glycosidic bond formation reactions. Unfortunately, not all glycals that would otherwise be suitable for a step-wise synthesis are readily available; i.e., the glycals are known or can be prepared, but are prepared with relative difficulty. This is particularly the case for glycals that are derivatives of the gulal and allal series of compounds, a gulal derivative being present in lasacoid A as well as being present in the sulfur substituent-containing glycoside present in the esperamicins and the calicheamicins.

It would therefore be beneficial if substituted gulal and allal compounds could be prepared so that such compounds could be used as intermediates in the preparation of lasacoid A, an esperamicin and/or a calicheamicin or a derivative thereof. The disclosure that follows describes a high yield synthetic procedure whereby such substituted gulal and allal compounds can be prepared.

SUMMARY

The present invention contemplates a method of forming a 3-axial-hydroxy allal or gulal derivative from a 3-equatorial glucal or galactal O-ester, respectively, and the products of the reactions utilized in that formation. In accordance with this method, a substituted glycal compounds having a 3-equatorial-O-ester group is reacted with an organothio, preferably having fewer than 15 carbon atoms in the organic radical, to form an o-thioorganopseudoglycal. The α-thioorganopseudoglycal is oxidized, preferably with a peroxide-type oxidant, to form the corresponding α-sulfoxidopseudoglycal. The o-sulfoxidopseudoglycal is then rearranged in the presence of a thiophile to form the corresponding 3-axial-hydroxy-glycal. Each of the intermediate products can be recovered, as desired.

The present invention has several benefits and advantages.

One benefit of the invention is that substituted 3-axial hydroxy glycal compounds can be prepared in relatively high yield from readily available glucal and galactal 3-equatorial ester precursors.

An advantage of the invention is that the substituted 3-axial hydroxy gulal and allal derivatives are prepared without substantial change to other substituent groups that are present on the starting materials.

Another advantage is that configurational changes of substituent groups other than the equatorial 3-position ester groups do not occur during formation of the 3-position axial hydroxyl.

Another benefit of the invention is that oligosaccharides containing saccharide units of the gulose and allose configuration as are present in antibiotics can be more readily prepared than by prior techniques.

Still further benefits and advantages of the invention will be apparent to the skilled worker from the disclosure that follows.

BRIEF DESCRIPTION OF THE DRAWINGS

In the drawings forming a portion of this disclosure,

FIG. 6 in two sheets (FIG. 6/1 and FIG. 6/2) illustrates a reaction scheme for the preparation of an esperamicin trisaccharide Compound 2a and a chimeric antibiotic that utilizes that trisaccharide, Compound 43. In this scheme, P$_1$ is 2,4-dinitrophenyl, R$_1$ is p-methoxybenzyl, OAc is acetate, MeI is methyl iodide, DDQ is 2,3-dichloro-5,6-dicyano-1,4-benzoquinone and ROH is an exemplary aglycone such as daunorubicin or doxorubicin aglycone.

DEFINITIONS

The following words and phrases are utilized herein to have the meanings that are normally recognized in the art and as are described below.

A "glycal" is a cyclic enol ether derivative of a sugar having a double bond between carbon atoms at positions 1 and 2 of the ring.

A glycal compound useful herein contains a chain of 5-9 carbon atoms and is in the form of a cyclic ring having 5 or 6 atoms that are members of the ring. A useful glycal compound also includes a plurality of substituent groups, and is thus referred to as a substituted glycal compound. Substituted glycal compounds are also referred to herein as "glycals" for greater ease of expression with the understanding that a substituted glycal compound is implied.

A "pseudoglycal" is a cyclic sugar ether derivative having a double bond between the carbon atoms of positions 2 and 3 of the ring.

The term "sugar" and "sugar derivative" are utilized herein generically to mean a carbohydrate or carbohydrate derivative that contains 5-9 atoms in its backbone chain, and those of interest herein can be a pentose, hexose, heptose, octulose or nonulose.

A "monosaccharide" is a simple sugar that cannot be hydrolyzed into smaller units.

An "oligosaccharide" is a compound sugar that yields two to about 10 molecules of simple monosaccharide on hydrolysis.

A "polysaccharide" is a compound sugar that yields more than 10 molecules of simple monosaccharide per molecule on hydrolysis.

A sugar molecule or its derivative typically contains a plurality of hydrogen, alkyl, hydroxyl, amine or mercaptan groups in free or protected form such as the N-phthalimido group or the S-acetyl group bonded to each of the carbon atoms of the molecular chain. Where the sugar molecule is in cyclic form, the oxygen atom of one of the hydroxyl groups is utilized as the oxygen that is part of the cyclic ring structure. A deoxysugar contains a hydrogen atom or other substituent group in place of one of the hydroxyl groups.

Each of the substituents, other than the hydrogen of a deoxysugar, has a particular stereochemical configuration relative to the other substituents and relative to the plane of the cyclic ring. The chain length and stereochemical configuration of the substituent groups provide the basis for the names of the sugars. The sugar molecules and their derivatives utilized herein are of known stereochemical configuration.

Position numbering in a sugar molecule begins with the aldehydic carbon for aldoses and the terminal carbon atom closest to the keto group for ketoses. Thus, for a glycal, the first carbon of the ethylenic unsaturation adjacent the ring oxygen is numbered "position 1", with the remaining positions being numbered around the ring away from the ring oxygen atom.

The carbon atom at position 1 is also referred to as the "anomeric atom" or "anomeric carbon atom" due to the possible formation of anomers at that position. Alpha ($\alpha$) anomers are bonded below the plane of the ring in its usually drawn form, whereas in beta ($\beta$) anomers, the bond is above the plane of the ring when so drawn. A substituent at other than the anomeric carbon atom can also be above or below the ring, and thus can also have a $\beta$ or $\alpha$ configuration.

In addition, a substituent can also be said to point sideways or outward from the ring while being held generally in the plane of a six-membered ring, and be in a so-called equatorial configurational position. A substituent can also be generally pointing up or down from the ring and be held at almost right angles to the ring, and said to be in an axial configurational position. A particularly preferred substituted glycal compound starting material utilized herein contains a six-membered ring and a substituent at the 3-position in the equatorial configuration, whereas a corresponding substituted glycal compound reaction product contains an oxygen substituent in the 3-position that is axially configured.

A "glycoside" is a sugar derivative containing a substituent bonded to the anomeric carbon atom. The glycosidic bond can be between the anomeric carbon and an oxygen, nitrogen or sulfur atom and their appropriate other substituents other than hydrogen.

The word "corresponding" is used herein in relation to substituted glycal compounds and their reaction products to mean that the substituents present on a reactant compound prior to a given reaction are present in the same configuration after the reaction unless otherwise stated. The word "corresponding" is used to further mean that except for a labile group such as an ester bonded to a given substituent that may be removed during a reaction, all of the substituents present on a reactant prior to a given reaction are present after that reaction has been completed, except where otherwise noted.

Thus, for example, where a methyl group, a non-labile group, is present prior to a reaction, that methyl group is present after completion of the reaction and is in the same stereoconfiguration after the reaction as it was prior to the reaction. On the other hand, an acetyl group bonded to a glycal ring oxygen atom can be a labile group and can be lost during a given reaction, whereas the non-labile glycal ring oxygen atom to which it was bonded remains present after the reaction and in its original stereoconfiguration. Still further, a whole ester group such as an acetoxy group can be replaced as is the case where a thioorganopseudoglycal is formed, but in such an instance, pseudoglycal formation is noted and it is to be understood that the entire ester group (e.g. an acetoxy group) has been replaced.

DETAILED DESCRIPTION OF THE INVENTION

A. Introduction

The advent of the potent DNA cutting antibiotics esperamicin and calicheamicin [(a) Lee, et al., *J. Am. Chem. Soc.*, 109,3464 (1987); and (b) Lee, et al., *J. Am. Chem. Soc.*, 109,3466 (1987)] raise numerous issues in biology and chemistry. Not the least of the challenges and opportunities for organic synthesis in this area is that of the carbohydrate sector, or portion.

Whereas the enediyne carbocyclic aglycone presumably serves as the source of the "chemical radiation" in cleaving the DNA, the carbohydrate ensemble appears to play an important role as a recognition marker for the oligonucleotide. [For a review of the seminal experiments involving the generation of aromatic 1,4-diyls from cis-enediynes see: (a) Bergmann, R.G., *Acc. Chem. Res.*, 6,25 (1973). For early applications of the generation of aromatic 1,4-diradicals to mimic the mode of action of the esperamicins and calicheamicins, see: (b) Magnus et al., *J. Am. Chem. Soc.*, 110,6921 (1988); (c) Magnus et al., *J. Am. Chem. Soc.*, 110,1626 (1988); (d) Nicolaou et al., *J. Am. Chem. Soc.*, 110,1626 (1988); (d) Nicolaou et al., *J. Am. Chem. Soc.*, 110,4866 (1988). For examples of the use of related 1,4-diyls, such as that derived from esperamicin, in DNA cleavage see: (e) Nicolaou et al., *J. Am. Chem. Soc.*, 110,7247 (1988); (f) Mantlo et al., *J. Org. Chem.*, 54,2781 (1989); (g) Zein et al., *J. Am. Chem. Soc.*, 111,6888 (1989); (h) Hawley et al, *Proc. Natl. Acad. Sci., USA*, 86:1105 (1989); (i) Zein et al., *Science*, 244:697 (1989); (j) Long et al., *Proc. Natl. Acad. Sci., USA*, 86:2, (1989) and (k) Sugiura et al., *Proc. Natl. Acad. Sci. USA*, 86:7672 (1989)].

The present invention is directed toward the synthesis of substituted allal and gulal derivatives. A sulfur-substituted gulose derivative is present in the carbohydrate portion of an esperamicin, and sulfur-substituted gulal derivative can be used to synthesize that carbohydrate molecules, and is illustrated herein. To this end, the synthesis of the hexose containing the thiomethyl group and a general method for the syntheses of gulal and allal glycals are described herein. A non-selective synthesis of the thiol analog of the thiomethyl monosaccharide was recently reported to form a mixture in which the thiol group was at the 3- or 4-positions [Scharf et al., *Tetrahedron Lett.*, 34:4505 (1989)].

Figure 5:
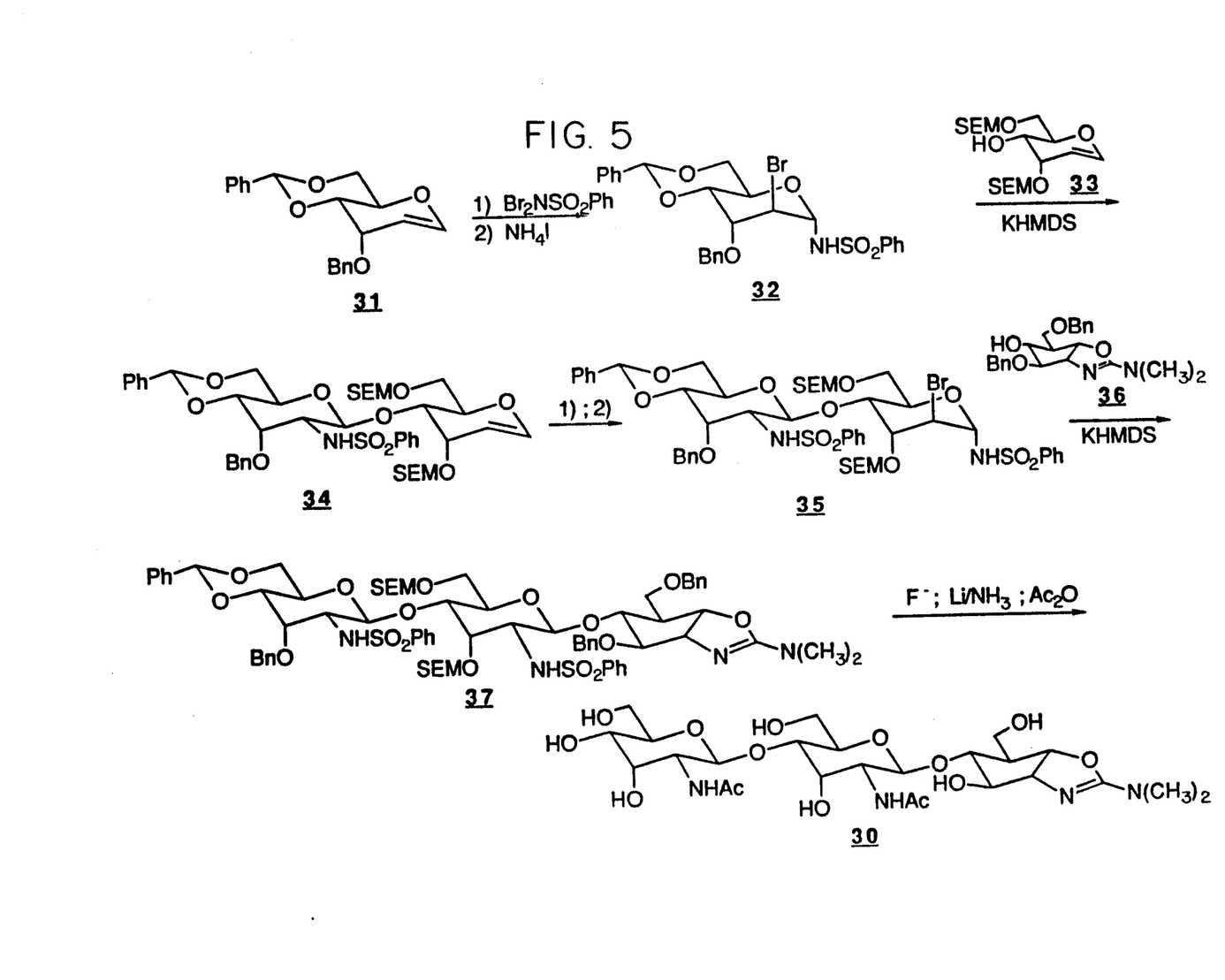
FIG. 5 illustrates a reaction scheme for the preparation of allosamidin, Compound 30, using substituted allal derivatives as are prepared herein. In this scheme, Ph is phenyl, Bn is benzyl, Br$_2$NSO$_2$Ph is N,N-dibromophenylsulfonamide, SEMO is trimethylsilylethoxymethoxy, KHMDS is potassium hexamethyldisilazide, Ac$_2$O is acetic anhydride, Ac is acetyl, F$^-$ is fluoride ion, and Li/NH$_3$ is lithium metal in liquid ammonia.

A still further use for a method and product of this invention is in the synthesis of allosamidin (Compound 30), a chitinase inhibitor. The structure of allosamidin is shown in FIG. 5, along with a synthetic scheme for its preparation.

Yet another use for the present invention is in the preparation of what can be called chimeric drugs. Such chimers contain a terminal glycoside bond formed from an anthracycline or other multiring or single ring structure aglycone and a glycal-terminated oligosaccharide. These drugs are referred to as chimeric because the aglycone portion and oligosaccharide portions are usually not found together in a naturally occurring drug. That is not to say, however, that a naturally occurring drug could not be made following the techniques described herein.

While the methyl glycoside Compound 3 was a particular focus of the present effort, a more general objective was that of providing access to glycals bearing 3-axial alcohol derivatives, with a range of substituents at the 4-position (C4). All attempted reductions of the corresponding 3-position ketones lead to equatorial alcohols [Danishefsky et al., *Angew. Chem.*, Int. Ed. Eng., 26:15 (1987)]. Attempts to directly invert the equatorial 3-OH using Mitsunobu conditions or by displacing equatorial leaving groups led only to Sn2' reactivity. [For some previous preparations of allal and gulal derivatives see: (a) Sharma et al., *Can. J. Chem.*, 44:2825 (1966); (b) Lemieux et al., *Can. J. Chem.*, 44:61 (1968); (c) Naden et al., *J. Am. Chem. Soc.*, 108:1155 (1980); and (d) Ireland et al., *J. Org. Chem.*, 45:48 (1980).]

Glycals of this type can be useful intermediates for reaching Compound 3 and can serve as glycosyl donors pursuant to a projected synthesis of the larger goal; i.e., the esperamicin trisaccharide (Compound 2) that itself can be linked to the substituted enediyne carbocylic portion of the molecule to form a synthetically produced esperamicin (Compound 1), or a derivative thereof that also binds to DNA.

B. The Method

The present invention contemplates a method for the preparation of a substituted glycal compound having the configuration of the gulal or allal series of glycals from a substituted glycal compound having the configuration of a galactal or a glucal series of glycals, respectively. Thus, the 3-equatorial ester group is displaced and replaced by an axial oxygen-containing substituent that forms a hydroxyl group so that the method inverts the configuration of the glycal 3-position oxygen atom derivative from the equatorial to the axial configuration. The resulting substituted glycal compound is useful for the preparation of an oligosaccharide as discussed elsewhere herein.

Mannos and glucose differ from each other only at the configuration about the 2-position carbon atom. The same is true for talose and galactose. Thus, a glucal could be named a mannal and a galactal could be named a talal as there are no configurational isomers at the 2-position of a glycal. The name glucal is utilized herein to encompass glucal and mannal, and the name galactal is used herein to encompass galactal and talal.

Similarly, allose and altrose differ only at the configuration about the 2-position carbon as do gulose and idose. Thus, an allal could be named an altral and a gulal could be named an idal. The name allal is utilized herein to encompass allal and altral, and the name gulal is used herein to encompass gulal and idal. Generalized configurational structures for an allal and a gulal series glycal are shown as Compounds 4 and 5, respectively.

In accordance with this method, a substituted glycal compounding having a 3-equatorial-O-ester group (an equatorial ester group) is reacted with an organothiol to form a corresponding α-thioorganpseudoglycal. The resulting α-thioorganopseudoglycal is oxidized to form the corresponding o-sulfoxidopseudoglycal. The α-sulfoxidopseudoglycal is reacted with a thiophile to form a corresponding glycal having a 3-position oxygen substituent in the axial configuration. The recovered 3-position oxygen substituent is usually a hydroxyl group, but can be an acyl ester when a 4-position substituent group is an O-acyl ester, and that group rearranges to form a 3-O-acyl-4-hydroxy derivative.

The 3-equatorial-O-ester groups contemplated are organic esters and preferably are $C_1-C_6$ lower alkyl ester groups such as formyl, acetyl, iso-butyryl, cyclopentanoyl and hexanoyl. However, aromatic ester groups such as benzoyl and substituted benzoyl such as toluyl and p-nitrobenzoyl, α- and β-naphthoyl and substituted naphthoyl esters containing up to 15 carbon atoms, as well as methane sulfonyl (mesyl), p-toluenesulfonyl (tosyl) esters and larger acyl groups are also contemplated. The 3-equatorial-O-ester group is thus a leaving group that is displaced when the 2-α-thioorganopseudoglycal is formed. An acetyl group and its 3-position bonded oxygen atom (an acetoxy group) is a preferred 3-equatorial-O-ester group.

The organothiol reagent can be substantially any organothiol having fewer than 15 carbon atoms, although an aromatic thiol such as benzenethiol (thiophenol) or a $C_1-C_6$ lower alkyl substituted thiophenol is preferred. The reactions described herein are typically carried out in etherial or halogenated solvents so that the organothiol, and the above 3-O-ester group, should be free from ionic charge so as to be soluble in the organic solvent utilized. Other organothiols that can be utilized include methanethiol α- or β-thionaphthol, as well as $C_1-C_6$ lower alkyl substituted thionaphthols. A thiophenyl group will be used hereinafter as exemplary.

Reaction of the organothiol with the reactant 3-β-(equatorial)-O-ester displaces the 3-position O-ester to form a corresponding o(axial)thioorganopseudoglycal. That is, the glycal double bond is moved from between the 1- and 2-positions to between the 2- and 3-positions, making the reaction product a 2-pseudoglycal. In addition, the thioorgano group is introduced into the 1-position and in the α- or axial-configuration. Using the exemplary thiophenol, an α-thiophenylpseudoglycal is formed.

The reaction of the 3-equatorial ester glycal and organothiol is carried out in a reaction mixture containing a solvent that is inert to the chemical reaction, as are preferably all of the solvents discussed herein. Preferred solvents for this reaction are relatively low boiling, e.g., below 100 degrees C. halogenated solvents such as dichloromethane, chloroform and dichloroethane, and ethers, such as diethyl ether and THF, and boron trifluoride-etherate. The reaction is typically carried out at a temperature of zero to about $-80$ degrees C. All reactions described herein are preferably carried out at ambient pressure.

The α-thiophenylpseudoglycal is thereafter oxidized to form a corresponding sulfoxide derivative, that can be named generally as a corresponding α-thiosulfoxidopseudoglycal. Peroxide-type oxidants are preferably utilized for this reaction an include hydrogen peroxide, peroxyacetic acid, benzoyl peroxide and the most preferred, m-chloroperoxybenzoic acid (MCPBA). Sodium periodate, sodium perborate and acyl nitrites can also be utilized. Care should be taken to avoid using an excess of the oxidizing agent to inhibit further reaction of the sulfoxide to a corresponding sulfone, as is well known.

The reaction mixture for the oxidation reaction typically contains a before-discussed halogenated solvent. The oxidation is carried out at a temperature of about zero to about $-40$ degrees C.

The resulting corresponding sulfoxide pseudoglycals can be isolated, but usually are not analyzed because they form an equilibrium mixture with the corresponding [2,3]-rearranged 3-axial-sulfenate glycal esters, and because diastersomers are formed. Interception of the sulfenate ester with a thiophilic reagent cleaves the sulfenate ester to form a corresponding 3-axial-hydroxy glycal. Formation of the desired 3-axial-hydroxy glycal shifts the equilibrium so that in usual practice, only the 3-axial-hydroxy glycal is observed.

Exemplary thiophilic reagents include a secondary amine such as a $C_2-C_{12}$ secondary amine like piperidine, dimethylamine and di-n-hexylamine, a tri-$C_1-C_6$ alkyl phosphite such as trimethyl phosphite, triethyl phosphite or trihexyl phosphite, an alkali metal $C_1-C_6$ thiolate such as sodium or lithium benzenethiolate or sodium methanethiolate, an alkali metal cyanoborohydride such as sodium or lithium borohydride, or a tri-$C_1-C_6$ alkylaminophosphene such a trimethylamino or triethyamino phosphene.

The resulting, corresponding 3-axial-hydroxy glycal can be isolated or recovered as such or can be reacted in situ as with an ester-forming agent such as acetic anhydride to form a substituted 3-axial-O-ester glycal compound product that is substantially identical to the starting substituted 3-equatorial-O-ester glycal compound except for the inverted stereochemistry of the 3-position oxygen atom. Of course, the 3-axial-hydroxyl group can also be reacted in other manners such as by alkylation to form an ether group such as a benzyl ether. Each of the before-discussed intermediates can also be, and preferably is, recovered.

The [2,3]-rearrangement reaction is typically carried out in methanol, ethanol, tetrahydrofuran (THF) or diethyl ether. This rearrangement reaction is carried out at a temperature of about zero to about 50 degrees C.

As already noted, a useful starting substituted glycal compound and a glycal reaction product are substituted cyclic sugar derivatives that contain a double bond between the carbon atoms at glycal ring positions 1 and 2. The glycal rings themselves contain five or six atoms including oxygen, whereas the chain that makes up the backbone of the sugar derivatives can have 5 through 9 carbon atoms.

A starting substituted glycal compound utilized herein can be prepared by well known techniques. Each of the starting substituted glycals utilized herein was available commercially. See also Danishefsky et al., *J. Am. Chem. Soc.*, 110: 3929 (1988), and the citations therein.

A useful glycal is referred to as being substituted. Cyclic sugar molecules are themselves hydroxyl-substituted tetrahydropyran or tetrahydrofuran derivatives. A useful glycal can therefore be considered to be a dihydropyran or a 2,3-dihydrofuran derivative. In view of the differing nomenclatures that can be utilized for sugar derivatives, and for clarity of expression, a hydroxyl group as would normally be present in a sugar molecule is referred to herein as a glycal substituent. Similarly, hydrogen, which is normally present on a dihydropyran or 2,3-dihydrofuran, but is a substituent that replaces a hydroxyl of a sugar, is also referred to herein as a substituent.

Each glycal thus has a plurality of substituent groups. Exemplary, useful substituent groups include hydrogen, hydroxyl, $C_1-C_6$ alkyl, as well as protected hydroxyl, protected mercaptan, amine, and protected amine groups. Of the above substituents, hydrogen, hydroxyl, $C_1-C_6$ alkyl and protected hydroxyl (O-ether or O-ester), protected mercaptan (S-ether or S-ester), and protected amine (amide or imide) groups are preferred.

Protected substituents are those that are reacted with another reagent to form a substituent that does not undergo reaction under the conditions of 3-position inversion or other reactions contemplated. A group is also considered protected if it reacts, but can be readily regenerated as by reduction or ester formation. Most preferably, as where a glycoside such as an oligosaccharide is to be prepared that does not have protecting groups, a preferred protecting group is readily removable to provide the unprotected substituent with little or no alteration of the stereochemical configuration of the substituent or glycoside bonds.

Various types of ether-forming readily removable protecting groups are preferred for hydroxyl substituents, so that the substituents themselves are ethers. Particularly preferred readily removable ether linkages are benzyl or ring-substituted benzyl ethers having 7–10 carbon atoms, diaryl-$C_1-C_6$ alkylsilyl ethers such as diphenylmethylsilyl ether, aryldi-$C_1-C_6$ alkylsilyl ethers such as a phenyldimethylsilyl ether, and tri-$C_1-C_6$ alkylsilyl ethers such as trimethylsilyl and t-butyldimethylsilyl ethers. Acetals and ketals are also considered to contain ether linkages since each contains the C-O-C bond of an ether. Acetals and ketals formed from an aldehyde or ketone containing 1 to about 12 carbon atoms such as formaldehyde, acetone, cyclohexanone, 1-decanal and 5-nonanone or an aromatic aldehyde such as benzaldehyde or naphthaldehyde or an aromatic ketone such as acetophenone are contemplated. Acetone, formaldehyde and benzaldehyde are preferred for the preparation of ketals and acetals, respectively. Additional useful readily removable protecting groups are discussed in Kunz, *Angew. Chem. Int. Ed. Engl.*, 26: 294 (1988), whose disclosures are incorporated by reference.

The above-described readily removable substituents can be removed by a number of means well known in the art. For example, the benzyl ether-type protecting groups can be removed by hydrogenolysis over a palladium catalyst or by sodium or lithium in liquid ammonia. The various silyl ethers can be removed by reaction with tetrabutylammonium fluoride. The acetals and ketals can be removed with mild acids.

A useful 3-equatorial-O-ester substituted glycal compound can itself also be a derivatized oligosaccharide whose terminal saccharide unit is a substituted glycal. Thus, an ether or other linkage can also be present between the reacting glycal unit and another derivatized monosaccharide or oligosaccharide. This linkage is preferably between the anomeric carbon atom of the substituent sugar derivative and the glycal unit, although such a glycosidic bond is not required. In this instance, the substituents on the glycal are as described before along with one or more derivatized saccharide units as further substituents; those derivatized saccharide substituents also having substituents as described before.

Thus, a substituted glycal can be a substituted glycal-terminated oligosaccharide. For example, a di- or tri-saccharide terminated with a glycal can itself be a starting substituted glycal useful herein.

It is neither always necessary nor desired that an ether substituent be readily removable. To that end, an O-ether or S-ether can contain a $C_1-C_{18}$ alkyl, $C_6-C_{10}$ aryl or substituted aryl or non-benzyl $C_7-C_{10}$ aralkyl group bonded through an oxygen atom to the ring of a derivatized sugar molecule. Exemplary of such groups are methyl, ethyl, iso-propyl, cyclohexyl, lauryl and stearyl ethers, as well as phenyl, p-tolyl, 2-naphthyl, ethylphenyl, and 4-t-butylphenyl ethers. Oligosaccharides are another group of ether substituents that are not readily removed.

Other groups include $C_1-C_6$ alkyl and hydrogen. Exemplary $C_1-C_6$ alkyl groups include methyl, ethyl, iso-propyl, sec-butyl, cyclopentyl and n-hexyl groups.

When the substituted glycal is oxidized to form a substituted 1,2-anhydrosugar as discussed in Halcomb et al., *J. Am. Chem. Soc.*, 111:6661 (1989), it is important that the substituents not also be oxidized, or if oxidized, be readily reduced back to the original substituent. To that end, acyl protecting groups such as those formed by the reaction of a hydroxyl, mercaptan or amine group with a $C_1-C_{18}$ a alkanoic acid such as acetic, stearic or cyclohexanoic acids or an aromatic acid such as benzoic, or 1-naphthaleneacetic acid (or formed from an anhydride, acid chloride or activated ester such as a N-hydroxysuccinimido ester of such an acid); i.e., a $C_1-C_{18}$ a acyl group, is also useful. A cyclic imide containing a total of 4–10 carbon atoms and 5–7 atoms in the imido ring such as succinimido, substituted succinimido such as methylsuccinimido, phthalimido or a substituted phthalimide like 4-chlorophthalimido and a cyclic amide having 4–10 carbon atoms and 5–7 atoms in the amido ring such as pyrrolidinyl, valerolactamyl or caprolactamyl are also useful.

A useful starting substituted glycal compound is a derivative of a glucal or a galactal that can be represented by the chemical formula wherein $R^1$ is in the equatorial configuration and is an O-ester group in which the acid portion is selected from the group consisting of $C_1-C_6$ lower alkyl, a substituted or unsubstituted aromatic group containing less than 15 carbon atoms, mesyl and tosyl;

$R^2$ is selected from the group consisting of H, $C_1$-$C_6$ alkyl, 2-furyl, $OR^4$, $NR^5R^6$ and $SR^6$;

$R^3$ is selected from the group consisting of H, $C_1$-$C_6$ alkyl, $(CH_2)_mOR^4$, 2-furyl, $OR^4$, $NR^5R^6$, $SR^6$, or $R^3$ and $R^2$ form a cyclic acetal or ketal prepared from an aldehyde or ketone containing 1 to 12 carbon atoms;

m is zero, 1, 2, 3 or 4 (1-4) with the proviso that the number of carbon atoms in the glycal chain is not greater than 9, such that when m is zero, $R^3$ is $OR^4$, whereas when m is 1-4, m represents the number of methylene groups present;

n is zero or 1 such that when n is zero $R^2CH$ is absent, and when n is 1 $R^2CH$ is present;

$R^4$ is selected from the group consisting of hydrogen, $C_1$-$C_{18}$ alkyl, $C_6$-$C_{10}$ aryl, $C_1$-$C_{18}$ acyl, $C_7$-$C_{10}$ aralkyl, tri-$C_1$-$C_6$ alkylsilyl, diaryl-$C_1$-$C_6$ alkylsilyl, aryldi-$C_1$-$C_6$ alkylsilyl, and a substituted mono- or oligosaccharide;

$R^5$ is selected from the group consisting of $C_1$-$C_{18}$ a alkyl, $C_6$-$C_{10}$ aryl, $C_7$-$C_{10}$ aralkyl, tri-$C_1$-$C_6$ alkylsilyl, aryl di-$C_1$-$C_6$ alkylsilyl, diaryl $C_1$-$C_6$ alkylsilyl, and $C_1$-$C_{18}$ acyl;

$R^6$ is selected from the group consisting of H, $C_1$-$C_{18}$ a alkyl, $C_7$-$C_{10}$ aralkyl, and $C_1$-$C_{18}$ acyl with the proviso that (a) at least one of $R^5$ or $R^6$ of $NR^5R^6$ and $SR^6$ is $C_1$-$C_{18}$ a acyl, or (b) $NR^4R^5$ together form a cyclic amide or imide containing five to seven atoms in the ring and a total of 4-10 carbon atoms;

$R^7$ and $R^8$ are independently H or $C_1$-$C_9$ alkyl with the proviso that the number of carbon atoms in $R^7$ plus those of $R^8$ is nine or fewer; and $R^9$ is selected from the group consisting of hydrogen (H), or $C_1$-$C_6$ alkyl, $CO_2R^4$, CN, $CH_2OR^4$, 2-furyl, $R^{10}$ is selected from the group consisting of hydrogen (H), 2-furyl, or $C_1$-$C_6$ alkyl.

A preferred $C_1$-$C_{18}$ alkyl group is a $C_1$-$C_6$ alkyl group. A preferred $C_1$-$C_{18}$ a acyl group is a $C_1$-$C_6$ acyl group.

It is noted that hydrogens are not shown bonded to the carbon atoms linked to $R^1$, $R^3$, $R^9$ and $R^{10}$ for purposes of clarity. Those hydrogen atoms are nevertheless present on the substituted glycal compound.

Examples of each of the above-described R groups, where the R can be more than a single group, are provided in the previous discussion. It is noted that for purposes of counting carbon atoms in a chain of a substituted glycal compound, $C_1$-$C_6$ alkyl and 2-furyl substituent groups are considered to be substituents and not part of the sugar backbone chain.

In preferred practice, the stereochemical configuration of each of the substituent groups is known at the time the substituted glycal compound is reacted to invert the configuration at the 3-position. It is also preferred that $R^9$ and $R^{10}$ be hydrogen. Those remaining substituents for the substituted glycal ($R^2$ and $R^3$) are preferably independently selected from the group consisting of hydrogen, $C_1$-$C_6$ alkyl, $CH_2OR^{12}$ where $R^{12}$ is selected from the group consisting of hydrogen $C_1$-$C_6$ alkyl, $C_1$-$C_6$ acyl, tri-$C_1$-$C_6$ alkylsilyl, aryldi-$C_1$-$C_6$ $C_6$ alkylsilyl, diaryl $C_1$-$C_6$ alkylsilyl and a substituted mono- or oligosaccharide, $SR^{13}$ where $R^{13}$ is selected from the group consisting of $C_1$-$C_6$ alkyl, $C_6$-$C_{10}$ aralkyl and $C_1$-$C_6$ acyl, and $OR^{12}$ where $R^{12}$ is defined immediately above. In the above formula, n is preferably 1 so that a preferred substituted glycal compound has a ring that contains six atoms.

Using the above chemical formula as a basis, an α-thioorganopseudogylcal can be represented by the chemical formula wherein n, $R^2$, $R^3$, $R^9$ and $R^{10}$ are as before defined, and $R^{11}$ is an organic radical having fewer than 15 carbon atoms that is preferably a phenyl or substituted phenyl such as tolyl or m-chlorophenyl, or a $C_1$-$C_6$ lower alkyl group.

The corresponding α-sulfoxidopseudoglycal can be represented by the chemical formula wherein n, $R^2$, $R^3$, $R^9$, $R^{10}$ and $R^{11}$ are as before defined.

A product of the method of this invention; i.e., a substituted allal or gulal derivative, also has a structure shown in the above chemical formula except that the former $R^1$ substituent has been converted into a hydroxyl group that is in the axial configuration. A product of this method can be generally represented by the chemical formula shown below wherein n, $R^2$, $R^3$, $R^9$ and $R^{10}$ are as before defined and the 3-position hydroxyl group is in the axial configuration.

C. Results

1. Monosaccharide Products

Figure 1:
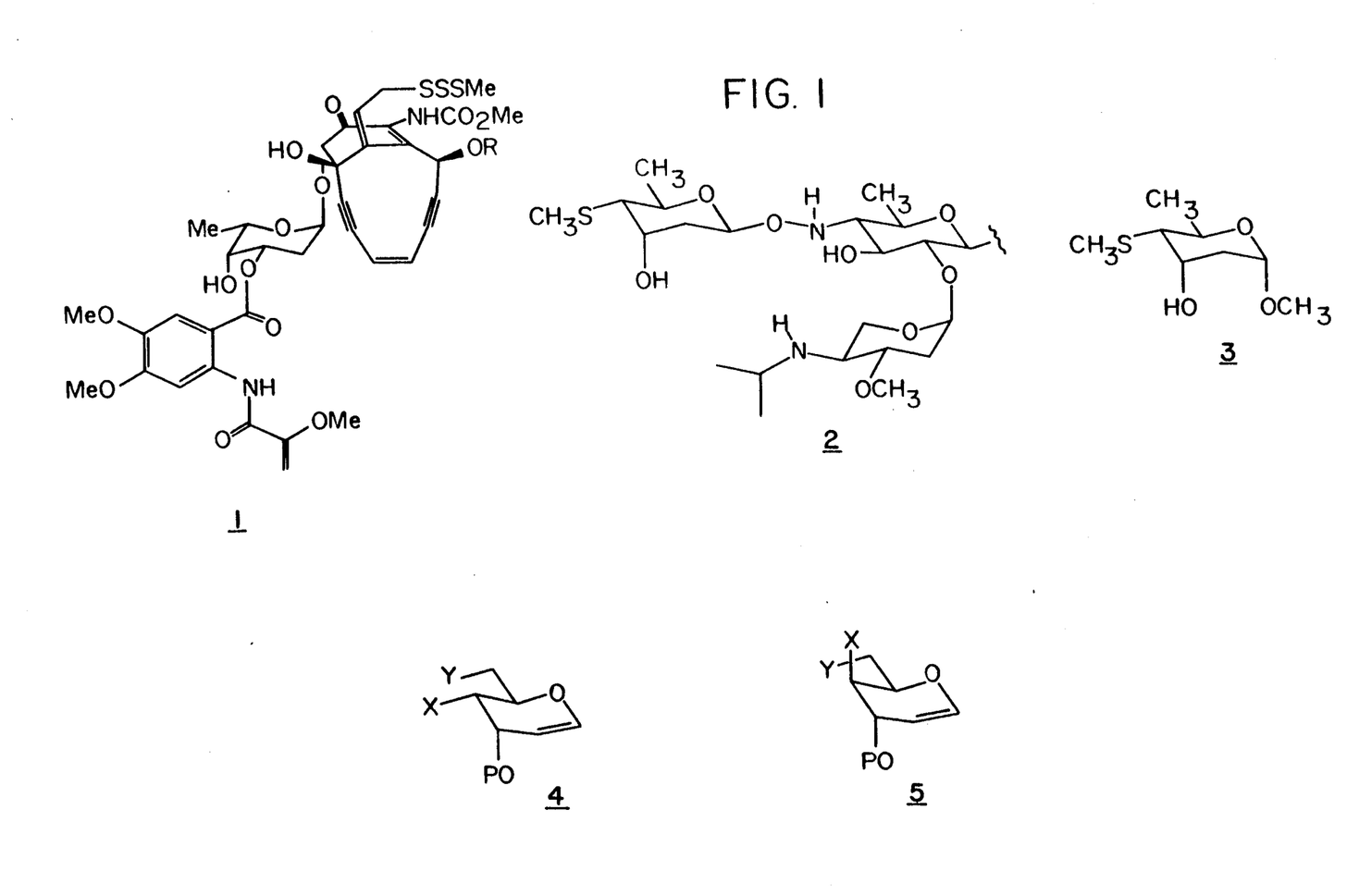
FIG. 1 illustrates compounds and compound types of interest to this invention. Compound 1 is an esperamicin and in the formula shown, Me is methyl and R is the esperamin trisaccharide, Compound 2. The wavy line shown for Compound 2 illustrates the point of attachment of the trisaccharide to the oxygen atom of the OR group of Compound 1. Compound 3 is the O-methyl glycoside of a terminal glycosidic group of Compound 2. Compounds 4 and 5 respectively illustrate generalized structures of allal and gulal series derivatives in which P, X and Y are hydrogen or another substituent group.
Figure 2:
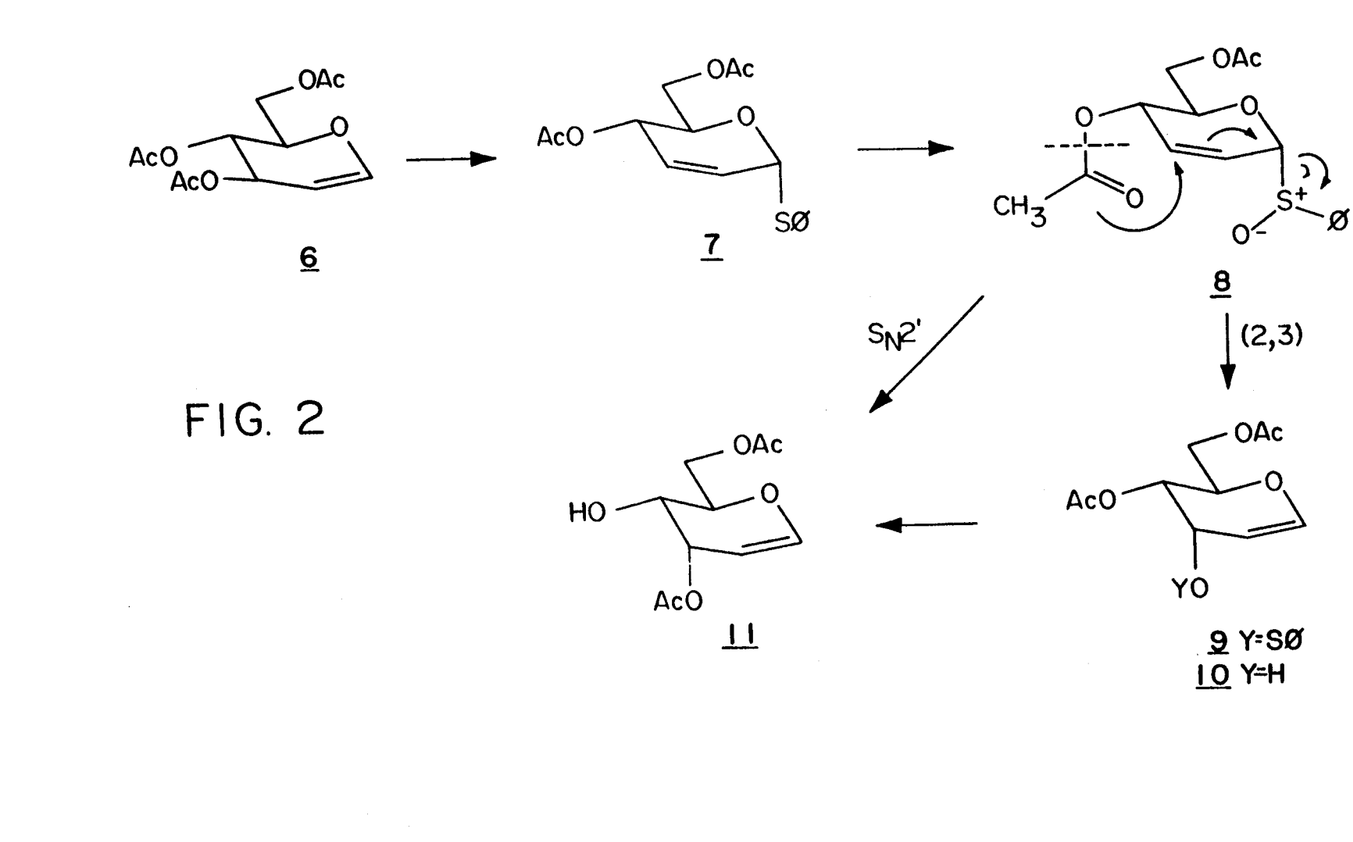
FIG. 2 illustrates a reaction scheme by which Compound 6 is converted successively to Compounds 7 and 8, and two possible mechanisms by which Compound 8 rearranges (is converted) to Compound 11. The first mechanism is an $S_N2'$ reaction, whereas the second is a [2,3]-rearrangement illustrated by [2,3]. In the structures, Ac is acetyl, $\phi$ is phenyl and Y of Compounds 9 and 10 is a substituent that can be $S\phi$ or H.

The method of this invention is well illustrated by the conversion of the commercially available triacetylglucal, Compound 6, to the allal derivative, Compound 11 (FIG. 2). Treatment of Compound 6 with benzenethiol (BF$_3$-etherate/methylene chloride $-78°$ C.) afforded by Ferrier-type rearrangement [(a) Ferrier et al., *J. Chem. Soc.,* C 1969:570, (b) Ferrier, *Adv. Carbohydr. Chem. Biochem.,* 25:199 (1969)] the α-thiophenylpseudoglycal Compound 7 in 72 percent yield [Valverde et al., *J. Chem. Soc., Chem. Commun.* 1987:383] in one synthesis. There was also produced about 8 percent of the corresponding β-thiophenyl anomer.

Figure 3:
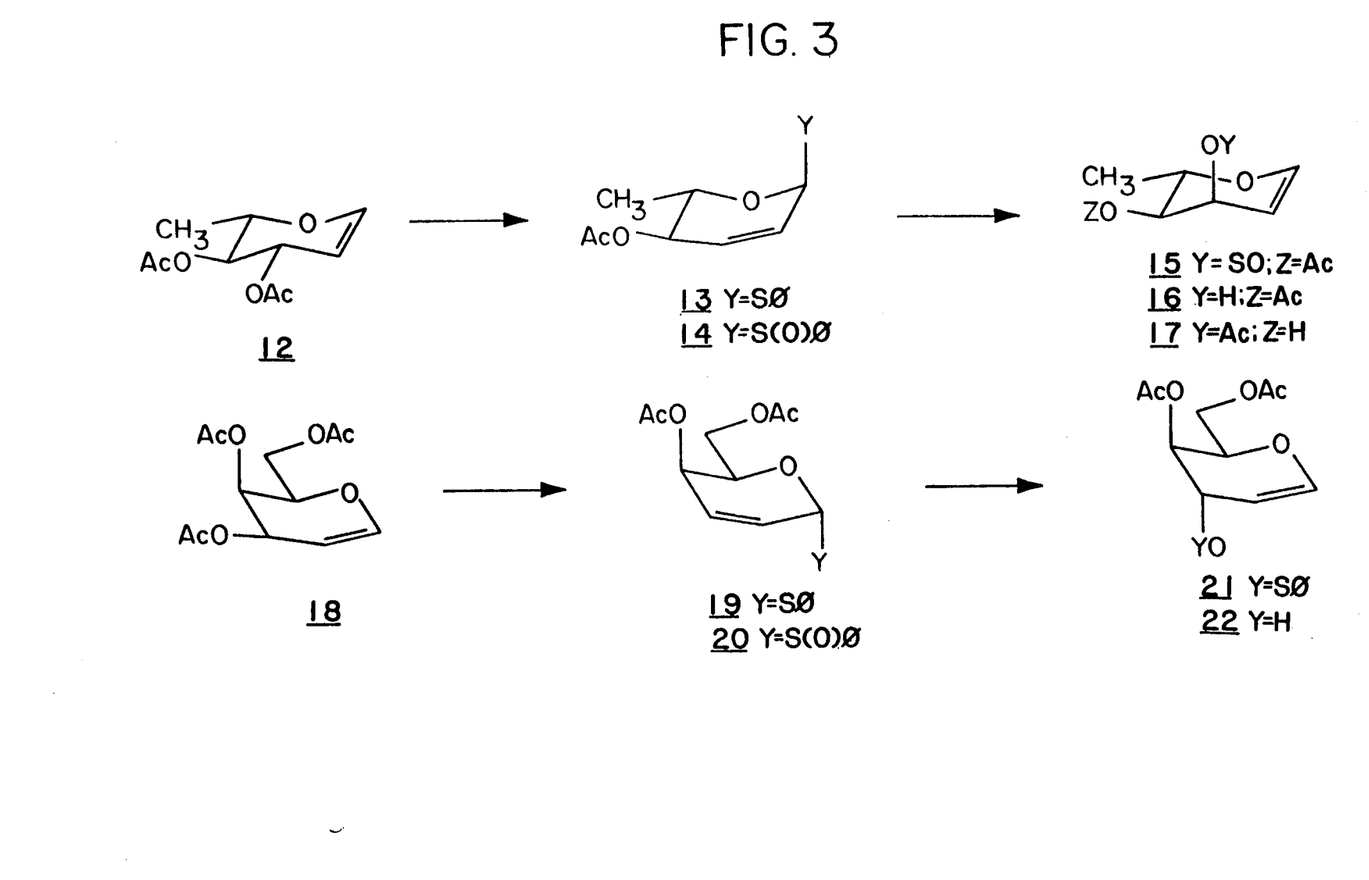
FIG. 3 illustrates reaction schemes for the conversion of Compound 12 to Compound 17 and conversion of Compound 15 to Compound 22. Ac is again acetyl, and Y and Z are substituents. For Compounds 13, 19 and 21, Y is $S\phi$, whereas for Compounds 14 and 20, Y is $S(O)\phi$. For Compound 15, Y is $S\phi$ and Z is Ac. For Compound 16, Y is H and Z is Ac. For Compound 17, Y is Ac and Z is H. Y is H in Compound 22.

Compound 7 was oxidized with m-chloroperoxybenzoic acid (MCPBA) in methylene chloride at zero degrees C. The sulfoxides were isolated but were not characterized. They were immediately treated with piperidine without any attempt to isolate their corresponding sulfenates. [For a striking demonstration of the lability of anomeric sulfoxides, see, Kahne et al., *J. Am. Chem. Soc.,* 111:6881 (1989).] Exposure of resultant sulfoxide Compound 8, to piperidine at room temperature afforded a 70 percent yield of Compound 11. In a similar way, L-rhamnal Compound 12 was converted to α-sulfide Compound 13 (71 percent yield), and thence to Compound 17 in 30 percent overall yield. (Complications arising from the volatility of glycal Compound 17 rather than differences in chemistry are responsible for the decreased yield in this case.)

All new compounds were characterized by IR and NMR spectroscopy, HRMS, and optical rotation with data provided hereinafter.

The most obvious formulation of these results involves [2,3] sigmatropic rearrangement of Compounds 8 (FIG. 2) and 14 (FIG. 3) [(a) Bickart et al., *J. Am. Chem. Soc.,* 90:4869 (1968); (b) Tang et al., *J. Am. Chem. Soc.,* 92:2100 (1970),] leading to sulfenate Compounds 9 and 15, respectively. These intermediates are interdicted with the thiophilic reagent piperidine to give Compound 10 and Compound 16. (via Compound 15), respectively, which undergo acyl transfer to provide the observed products Compounds 11 and 17, respectively.

An alternate formulation, which avoids the need to invoke an acyl transfer, contemplates neighboring group participation by the trans-disposed acetoxyl functions in Compounds 8 and 14, followed by solvolysis of the respective acetoxonium species. [A problem with the simple acetoxonium mechanism is that glycal formation is not noted until thiophile, either secondary amine or phosphite, is added (a) Evans et al., *J. Am. Chem. Soc.,* 93:4956 (1971); (b) Evans et al., *J. Am. Chem. Soc.,* 94:3672 (1972); and (c) Evans et al., *Acc. Chem. Res.,* 7:147 (1974).]

That the [2,3]-rearrangement mechanism is viable in other cases is seen from the transformation of D-galactal triacetate Compound 18 to the gulal derivative Compound 22 (60 percent overall) via the sulfide Compound 19 and the corresponding sulfoxide Compound 20 (FIG. 3). In this instance, no acyl transfer is observed and the process is well accommodated by proposing rearrangement of sulfoxide Compound 20 and interdiction of sulfenate ester Compound 21.

Figure 4:
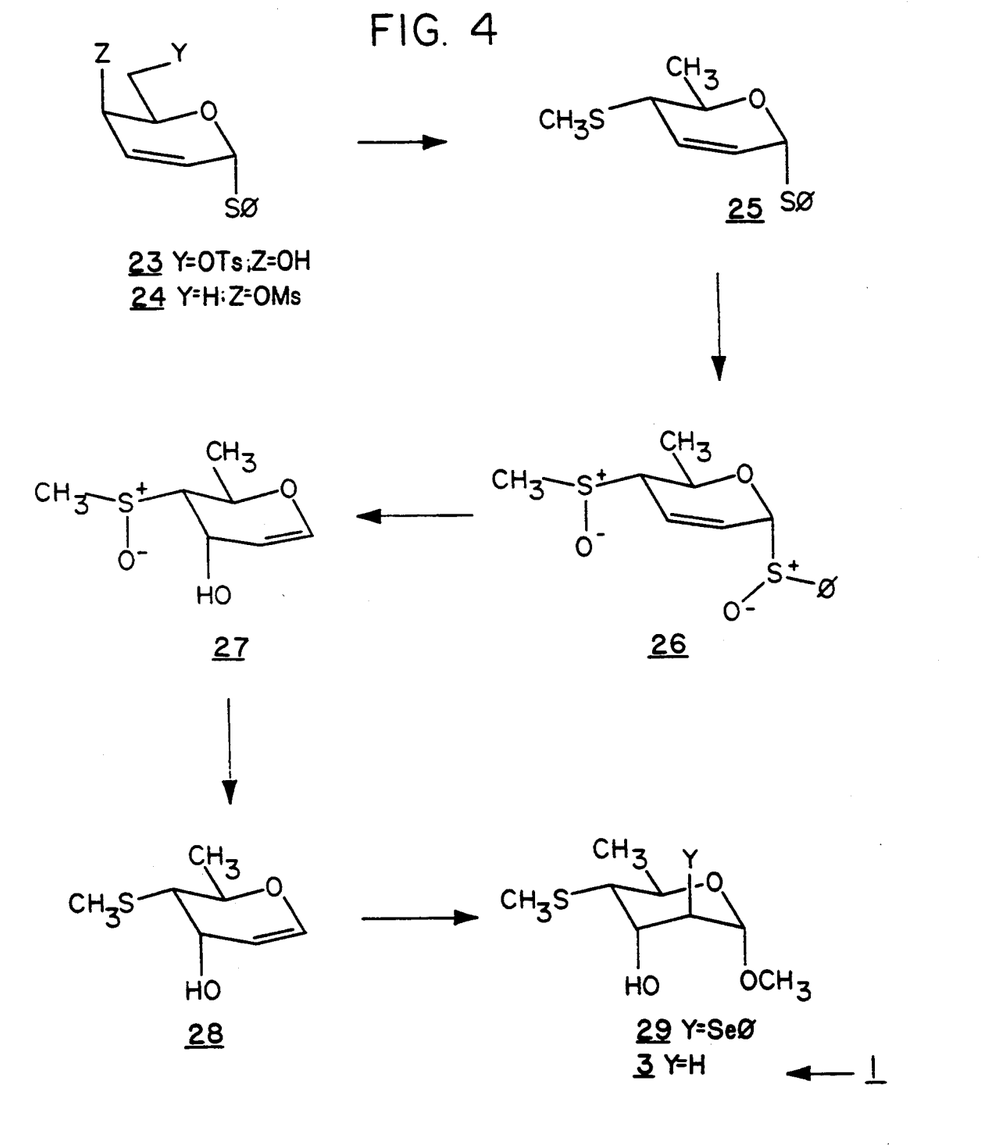
FIG. 4 illustrates a reaction scheme for the preparation of Compound 3 starting from Compound 23 at the top of the figure and Compound 1 at the bottom. For Compound 23, Y is O-tosyl (OTs) and Z is OH. For Compound 24, Y is H and Z is O-mesyl (OMs). For Compound 29, Y is Se$\phi$, whereas for Compound 3, Y is H.

The scope of the new glycal synthesis using more complex substituents has also been illustrated in reaching the desired target system, Compound 3 as is shown in the reaction scheme of FIG. 4. For this purpose, the galactal-derived sulfide, Compound 19, was utilized.

Two-fold deacetylation (sodium methoxide-methanol at room temperature) was followed by treatment with di-n-butylstannoxide and tosyl chloride in chloroform. There was thus obtained a 60 percent yield, the monotosylate derivative, Compound 23.

Reduction of Compound 23 with lithium aluminum hydride followed by mesylation afforded Compound 24. The bis thio Compound 25, whose 4-position configuration was inverted, was obtained (70 percent overall from Compound 23) upon reaction of Compound 24 with sodium methanethiolate.

Reaction of Compound 25 with 2.1 equivalents of MCPBA followed by exposure of the bis sulfoxide Compound 26 to the thiophile diethylamine to hydrolyze the 3-axial-sulfenate ester rearranged product afforded monosulfoxide Compound 27. It is noted that the rate of [2,3]-rearrangement [(a) Bickart et al., *J. Am. Chem. Soc.,* 90;4869 (1968); (b) Tang et al., *J. Am. Chem. Soc.,* 92:2100 (1970); (c) Evans et al., *J. Am. Chem. Soc.,* 93:4956 (1971); (d) Evans et al., *J. Am. Chem. Soc.,* 94:3672 (1972); and (e) Evans et al., *Acc. Chem. Res.,* 7:147 (1974),] of the anomeric phenysulfinyl function of Compound 26 is apparently much more rapid than is the potentially competing reaction of the methanesulfinyl group. The anomeric effect would favor rearrangement in the observed sense, Curran et al., *J. Am. Chem. Soc.,* 106:5002 (1984). Moreover, the rate of the observed [2,3]-process may be further enhanced by virtue of the axial character of the phenysulfinyl group as opposed to the equatorial nature of the methanesulfinyl unit.

Glycal Compound 28 (64 percent overall from Compound 25) was obtained by reduction of Compound 27 with lithium aluminum hydride. Methoxyselenation of Compound 28 afforded Compound 29, which upon reduction with triphenylstannane-azobisisobutyronitrile, provided the methyl glycoside Compound 3 (53 percent overall from Compound 28). For examples of the synthesis of 2-deoxy glycosides from glycals, see: (a) Lemieux et al., *Can. J. Chem.,* 42:539 (1964); (b) Lemieux et al., *Can. J. Chem.,* 42:547 (1964); (c) Thiem, *Trends in Synthetic Carbohydrate Chemistry,* Horton et al., eds., ACS Symposium Series 386, American Chemical Society, Washington, D.C., (1989); Chapter 8 and citations therein; (d) Jaurand et al., *J. Chem. Soc.,* Chem. Commun. 1981:572; (e) Jaurand et al., *J. Chem. Soc., Chem. Commun.* 1982:701; and (f) Beau et al., *Tetrahedron Lett..* 1987:1105.

The same compound was obtained by treatment of esperamicin with methanolic HCl (FIG. 4). The nmr spectra (300 MHz) and optical rotations [synthetic sample [α]D (CHCl$_3$, c, 0.61) $+270°$ C.; degradation product [α]D (CHCl$_3$, c, 0.275) $+273°$ C.] are the same.

In summary, a new route to glycals of the type of Compounds 4 or 5 has been developed. The method has been applied to the synthesis of glycal Compound 28, an intermediate that can be used for the total synthesis of the esperamicin trisaccharide, Compound 2. Methoxyselenation-reduction was used to convert Compound 28 to the α-methylglycoside Compound 3, obtained by degradation of esperamicin (a) Golik et al., *J. Am. Chem. Soc.,* 109:3461 (1987); and (b) Golik et al., *J. Am. Chem. Soc.,* 109:3462 (1987). This synthesis rigorously establishes the absolute configuration of the thiosugar residue of esperamicin.

2. Oligosaccharide Products

The before-illustrated syntheses of monosaccharide substituted glycal compounds can be utilized for the preparation of an oligosaccharide that contains a substituted allal or gulal derivative compound as illustrated hereinafter.

a. Synthesis of Allosamidin

In an exemplary synthesis of allosamidin, a synthetic scheme for which is shown in FIG. 5, the formed axial hydroxyl group of the allal derivative, Compound 10, is benzylated (Bn group) and the two acetyl groups removed and replaced by a benzylidene group to form Compound 31. The resulting Compound 31 is reacted with N,N-dibromobenzenesulfonamide in dichloromethane and then with ammonium iodide in ethanol to form the 2-benzenesulfonamide-3-bromo derivative, Compound 32.

Reaction of Compound 32 with Compound 33 (available from Compound 11 by standard procedures, and where SEMO is trimethylsilylethoxymethoxy) in the presence of potassium hexamethyldisilazide (KHMDS) in dimethyl formamide (DMF) at −40 degrees C., warming to room temperature, affords the disaccharide, Compound 34. Reaction of Compound 34 under the same two step reaction conditions [1); 2)] used to form Compound 32 affords Compound 35.

Reaction of Compound 35 with the glucosamine derivative Compound 36 provides the protected allosamidin derivative, Compound 37. Deprotection (removal) of the phenylsulfonamide group with fluoride ion and the benzylidene, benzyl and SEMO protecting groups with lithium in liquid ammonia, followed by acetylation with acetic anhydride provides allasamidin, Compound 30.

b. Synthesis of Esperamicin Glycoside and Chimeric Antibiotic

The synthesis of the esperamicin glycoside and an exemplary chimeric drug containing that glycoside are shown schematically in FIG. 6.

Here, Compound 38, wherein $P_1$ is 2,4-dinitrophenyl, that is prepared similarly to Compound 28 herein is reacted with disaccharide Compound 39, wherein $R_1$ is p-methoxybenzyl in the presence of mercuric acetate (Hg(OAc)$_2$) to form trisaccharide Compound 40. [The formation of the hydroxylamino group in a similarly substituted disaccharide is described in Wittman et al., J. Org. C... '981 (March, 1990).]

...pound 40 with 1,3-dimercaptopro... of sodium bicarbonate, followed ...hyl iodide in sodium hydroxide ...e thiomethyl ether, Compound ...limido group of Compound 41 ...by reductive alkylation of the ...ne and sodium cyanoborohy-...yl trisaccharide, Compound ...xybenzyl protecting groups ...dicyano-1,4-benzoquinone ...speramicin trisaccharide, ...haride, Compound 2%a, ...d with an aglycone to form a ...s, reaction of the trisaccharide Compound 2a with sodium hydride in trichloroacetonitrile, followed by reaction in boron trifluoride-etherate with an aglycone of another drug (ROH) such as daunorubicin or dioxorubicin aglycone, another anthracycline or the esperamycin aglycone forms the antibiotic chimeric drug shown as Compound 43. Glycosylation of oligosaccharides using sodium hydride and trichloroacetonitrile followed by reaction of the resulting activated oligosaccharide with various alcohols in boron trifluoride-etherate is reviewed in Schmidt, Angew. Chem. Int. Ed., Engl.), 25:212 (1986).

BEST MODE FOR CARRYING OUT THE INVENTION

The following examples illustrate the method and preparation of producing this invention.

EXAMPLE 1:

Phenyl 4,6-di-O-acetyl-2,3-dideoxy-1-thio-α-D-threo-hex-2-enopyranoside (Compound 19)

To a solution of tri-O-acetyl galactal Compound 18 (2.85 g, 10.5 mmol) in 130 mL of CH$_2$Cl$_2$ was added thiophenol (2.2 μL, 21.3 mmol). The reaction mixture was cooled to −15° C. and a solution of SnCl$_4$ added over 30 minutes (8 mmol, 0.8 M in CH$_2$Cl$_2$). The reaction mixture was washed with saturated NaHCO$_3$ and dried over MgSO$_4$. The solution was concentrated in vacuo and purified by silica gel chromatography (7:1→5:1 hexanes/ethyl acetate) to give 2.97 g of a white solid (88 percent) which by $^1$H NMR was a 5.3:1 mixture of α and β anomers.

mp 92°-93° C.; $[\alpha]_D^{25}$ +67.5° (CHCl$_3$, c, 5.2); IR (CHCl$_3$): 1730, 1365, 1215, 1065 cm$^{-1}$; $^1$H NMR (250 MHz, CDCl$_3$): δ 7.53 (m, 2H), 7.25 (m, 3H), 6.19 (dd, 1H, J=10.0, 3.2Hz), 6.06 (ddd, 1H, J=9.9, 5.3, 1.6 Hz), 5.81 (dd, 1H, J=3.2, 1.6 Hz), 5.09 (dd, 1H, J=5.3, 2.5 Hz), 4.66 (dt, 1H, J=6.4Hz), 2.04 (s, 3H), 1.99 (s, 3H); $^{13}$C NMR (62.9 MHz, CDCl$_3$) δ, 170.2, 134.6, 131.7, 131.2, 128.8, 127.5,. 124.4, 83.3, 67.2, 63.2, 62.6, 20.7, 20.6; HRMS (CI) M+H calcd for C$_{16}$H$_{18}$SO$_5$: 323.0954. Found: 323.0969.

EXAMPLE 2:

Phenyl-6-0-tosyl-2,3-dideoxy-1-thio-α-D-threo-hex-2-enopyranoside (Compound 23).

To a solution of the thioglycoside Compound 19 (2.17 g, 6.73 mmol) in 75 mL of methanol was added a 25 percent solution of sodium methoxide in methanol (MeOH; 0.10 mL). After stirring for one hour, the solution was neutralized with solid NH$_4$Cl and concetrated in vacuo. The residue was filtered through silica gel (2:1 hexanes/ethyl acetate) to give the diol as a white solid.

The diol was taken up in 100 mL of MeOH and refluxed for five hours with Bu$_2$SnO (bu=butyl; 2.35 g, 9.44 mmol). The solution was concentrated in vacuo and redissolved in 75 mL of CHCl$_3$. Tosyl chloride (2.0 0g, 10.5 mmol) was added at ambient temperature, and the solution stirred for four days.

The solution was washed with saturated NaHCO$_3$, dried over MgSO$_4$ and concentrated in vacuo. The residue L was then chromatographed over silica gel (2:1→1:1 hexanes/ethyl acetate) to give 2.18 g of the montosylate Compound 23, as a white solid (82 percent). mp 104°-105° C.; $[\alpha]_D^{25}$+111.9° (CHCl$_3$, c, 1.2); IR (CHCl$_3$) 3795, 1655, 1425, 1240, 1125, 1035 cm$^{-1}$; $^1$H NMR (250 MHz, CDCl$_3$) δ 7.76 (d, 2H, J=8.3Hz), 7.56 (m, 2H), 7.30 (m, 5H), 6.07 (m, 2H), 5.67(s, 1H), 4.59 (m, 1H), 4.36 (dd, 1H, J=10.7, 4.6), 4.19 (dd, 1H, J=10.7, 7.7Hz), 3.89 (br s, 1H), 2.43 (s, 3H); $^{13}$C NMR (62.9 MHz, CDCl$_3$) δ 144.9, 134.1, 132.7, 132.6, 129.8, 129.5, 128.9, 127.9. 127.8. 83.9, 69.0, 68.9, 61.6, 21.6; HRMS (CI) M+H calcd for C$_{19}$H$_{20}$S$_2$O$_5$: 393.0831. Found: 393.0819.

EXAMPLE 3

Phenyl-1-thio-4-methylthio-2,3,4,6-tetradeoxy-α-D-erythro-hex-2-enopyranoside (Compound 25)

To a suspension of lithium aluminum hydride (LAH) (135 mg, 3.55 mmol) in 10 mL of anhydrous tetrahydrofuran (THF) at reflux was added a 10 mL THF solution of the monotosylate Compound 23 (700 mg, 1.78 mmol). The solution was heated for one hour and then cooled to zero degrees C. The excess LAH was quenched 0.15 mL of water then 0.15 mL of 1N NaOH and finally with 0.30 mL of brine. The solution was dried with $MgSO_4$ and filtered. The solution was concentrated in vacuo and the residue dissolved in 20 mL of $CH_2Cl_2$.

The solution was cooled to zero degrees C. and triethylamine (0.75 mL, 5.34 mmol) and mesyl chloride added (0.21 mL, 2.71 mmol). After 30 minutes at zero degrees C., the solution was diluted with $CH_2Cl_2$ and washed with saturated $NaHCO_3$, dried over $MgSO_4$ and concentrated in vacuo.

The residue was taken up in 10 mL of methanol and treated with sodium methanethiolate (190 mg, 2.71 mmol). The solution was stirred for one hour, diluted with ether and washed with water and brine. The organic fraction was dried over $MgSO_4$, concentrated in vacuo and the residue chromatographed over silica gel (10:1 hexanes/ethyl acetate) to give 313 mg of the bis sulfide Compound 25 (70 percent).

[α $D^{25}$ +456° ($CHCl_3$, c, 6.5); 1R ($CHCl^3$) 1090 $cm^{-1}$; $^1$H NMR (250 MHz, $CDCl_3$) δ 7.53 (m, 2H), 7.30 (m, 3H), 6.11 (ABq, 1H, J=3.4, 2.4 Hz), 6.07 (ABq, 1H, J=3.4, 2.4 Hz), 5.92 (t, 1H, J=1.8 Hz), 5.89 (t, 1H, J=1.8 Hz), 5.71 (m, 1H), 4.30 (dq, 1H, J=9.8, 6.2 Hz), 3.06 (dq, 1H, J=9.8, 2.4 Hz), 2.07 (s, 3H), 1.46 (d, 3H, J=6.2 Hz); $^{13}$C NMR (62.9 MHz, $CDCl_3$) δ 135.8, 131.3, 130.3, 128.8, 128.2, 127.1, 83.3, 66.5, 45.3, 19.3, 11.1; HRMS (CI) M+H calcd for $C_{13}H_{16}S_2O$: 253.0722. Found: 253.0731.

EXAMPLE 4

1,5-anhydro-2,4,6-trideoxy-4-methythio-D-ribo-hex-1-enopyranose (Compound 28)

To a solution of the bis sulfide Compound 25 (50 mg, 0.198 mmol) in 3 mL of $CH_2Cl_2$ at zero degrees C. was added a solution of m-chloroperbenzoic acid (MCPBA) in $CH_2Cl_2$ (85 mg, 0.39 mmol, 0.20 M). After 30 minutes at zero degrees C., the reaction mixture was filtered, concentrated in vacuo and redissolved in 3 mL of THF. To a solution of the bis sulfoxide in THF was added diethylamine (0.15 mL, 1.45 mmol), followed by stirring for one hour. The solution was concetrated in vacuo and the residue chromatographed over silica gel (98:2 ethyl acetate/methanol) to give the rearranged sulfoxide.

The methyl sulfoxide was dissolved in 4 mL of THF and LAH added (10 mg, 0.263 mmol). After stirring for 24 hours, the solution was quenched by addition of 0.010 mL of water, 0.010 mL of 1N NaOH and 0.030 mL of brine. $MgSO_4$ was added and the solution filtered. The filtrate was concentrated in vacuo and the residue chromatographed over silica gel (3:1 hexanes/ethyl ether) to give 21 mg of the glycal Compound 28 (66 percent).

[α]$D^{25}$ + 170° ($CHCl_3$, c, 1.8); 1R ($CHCl_3$) 3600, 1650, 1575, 1475, 1430, 1100, 1045, $cm^{31 1}$; $^1$H NMR (250 MHz, $CDCl_3$) 6.48 (d, 1H, J=6.0 Hz), 5.02 (t, 1H, J=6.0 Hz), 4.14 (m, 1H), 4.02 (dq, 1H, J=11.0, 5.9 Hz), 2.70 (dd, 1H, J=10.6, 3.2 Hz), 2.61 (d, 1H, J=3.0 Hz), 2.19 (s, 3H), 1.46 (d, 3H, J=6.4 Hz); $^{13}$C NMR (62.9 MHz, $CDCl_3$) δ 146.5, 128.3, 101.3, 70.4, 60.2, 54.8, 19.3; HRMS (CI) M+H calcd for $C_7H_{12}SO_2$: 161.0637. Found: 161.0632.

EXAMPLE 5

Methyl 2,4,6-trideoxy-4-methylthio-α-D-ribo-hexopyranoside (Compound 3)

To a solution of the glycal Compound 28 in 5 mL of toluene at zero degrees C. was added sym-collidine (0.020 mL, 0.151 mmol), methanol (0.030 mL, 0.73 mmol) and phenylselenyl chloride (25 mg, 0.130 mmol). The solution was stirred 30 minutes at zero degrees C., diluted with ether, washed with saturated $NaHCO_3$, and dried over $MgSO_4$. The solution was concentrated and the methyl glycosides isolated by silica gel chromatograph (10:1 pentane/ether) to give 22 mg of the seleno α-methyl glycoside and 1.9 mg of the seleno β-methyl glycoside (77 percent).

To a solution of the seleno α-methyl glycoside in 4 mL of toluene was added triphenylstannane 930 mg, 0.085 mmol) and azo-bisisobutyronitrile (AIBN) (2 mg), and the solution was refluxed for 30 minutes. The solution was cooled, concentrated in vacuo and the residue chromatographed over silica gel (2:1 pentane/ether) to give 8 mg of the α-methyl glycoside Compound 3 as fine white needles (71 percent). mp 53°-54° C.; [α]D +233° ($CHCl_3$, c, 0.21); 1R ($CHCl_3$) 3457, 1125, 1095, 1055 $cm^{-1}$; $^1$H NMR (250 MHz, $CDCl_3$) δ 4.82 (d, 1H, J=3.6Hz), 4.10 (m, 1H), 4.02 (dq, 1H, J=10.7, 6.2 Hz), 2.51 (d, 1H, J=8.7Hz), 3.39 (s, 3H), 2.40 (dd, 1H, J=10.7, 2.6 Hz), 2.19 (s, 3H), 2.14 (brd, 1H, J=14.4 Hz), 1.92 (dt, 1H, J=14.4, 3.6 Hz), 1.40 (d, 3H, J=6.3 Hz).

EXAMPLE 6

Compound 7

Boron trifluoride-etherate (20 μl) was added to a solution of tri-O-acetyl-D-glucal (Compound 6; 109 mg) and thiophenol (300 μL) in $CH_2Cl_2$ (1.5 mL) at zero degrees C. The reaction mixture was stirred for 15 minutes at zero degrees C. and then quenched with 3 mL saturated $NaHCO_3$. The mixture was added to 25 mL $CH_2Cl_2$, which was then washed with 2×10 mL saturated $NaHCO_3$. The organics were dried over $MgSO_4$ filtered, and concentrated under reduced pressure. The residue was chromatographed on silica gel, eluting the hexane/ethyl acetate 9:1 to 3:1, to afford 93.3 mg of Compound 7, along with 10.3 mg of the corresponding β anomer.

EXAMPLE 7:

1,5-Anhydro-3,6-di-O-acetyl-2-deoxy-D-ribo-hex-1-enopyranose (Compound 11)

Compound 7 (31.2 mg) was dissolved in $CH_2Cl_2$ (1.0 mL) and the resulting reaction mixture solution was cooled to zero degrees C. Solid MCPBA (20.1 mg) was added and the mixture was stirred at zero degrees C. for 20 minutes. The mixture was added to 25 mL saturated $NaHCO_3$, which was then extracted with 3×10 mL ethyl acetate (EtOAc). The organics were dried over $MgSO_4$, filtered, and concentrated under reduced pressure. The residue was dissolved in MeOH (1.0 mL) to form a further reaction mixture and trimethyl phosphite (100 mL) was added. After stirring for 1.5 hours, the mixture was added to 25 mL saturated NaHCO₃ and extracted with 3×10 mL EtOAc. The organics were dried over MgSO₄, filtered, and concentrated. The residue was chromatographed on silica gel, eluting with hexane/EtOAc 1:1), to give 15.5 mg of Compound 11.

[α]D²⁵ +298° (CHCl₃, c, 1.350); IR (CHCl₃) 3580, 3030, 2960, 1740, 1645, 1375, 1240, 1100; cm⁻¹, ¹H NMR (250 MHz, CDCl₃) δ 6.51 (d, 1H, J=5.92), 5.25 (dd, 1H, J= 5.76, 3.99), 4.97 (t, 1H, J=12.33, 2.18), 4.41 (dd, 1H, J=12.32, 4.39), 4.04 (ddd, 1H, J=10.71, 4.30, 2.26), 3.95 (m, 1H), 2.71 (m, 1H), 2.13 (s, 3H), 2.12 (s, 3H); ¹³C NMR (62.9 MHz, CDCl₃) δ 171.30, 171.20, 147.8, 97.5, 72.8, 65.8, 52.5, 62.9, 21.2, 20.8; HRMS (Cl): M+H calcd for C₁₀H₁₅O₆: 231.0868. Found: 231.0861.

EXAMPLE 8

Phenyl 4-O-aoetyl-1-thio-2,4,6-trideoxy-α-L-erythro-hex-2-enopyranoside (Compound 13)

Boron trifluoride-etherate (20 μL) was added to a solution of di-O-acetyl-L-rhamnal (Compound 12; 101 mg) and thiophenol (300 μL) in 1.5 mL CH₂Cl₂ at zero degrees C. The solution was stirred for 15 minutes at zero degrees C. and quenched with 3 mL saturated NaHCO₃. The mixture was then added to 25 mL CH₂Cl₂ and washed with 2×10 mL saturated NaHCO₃. The organics were dried over MgSO₄, filtered, and concentrated under reduced pressure. The residue was chromatographed on silica gel, eluting with hexane/EtOAc 9:1, to give 72 mg of Compound 13.

[α]D²⁵ −337.6. (CHCl₃, c 1.525); IR (CHCl₃) 3020, 1740, 1480, 1440, 1375, 1245, 1095, 1065, 1045, cm⁻¹; ¹H NMR (250 MHz, CDCl₃) δ 7.53–7.45 (m, 2H), 7.34–7.21 (m, 3H), 6.01, (ddd, 1H, J=10.05, 3.06, 1.95), 5.81 (dt, 1H, J=10.09, 1.65), 5.70 (m, 1H), 5.14 (dq, 1H, J=9.07, 1.91), 4.26 (dq, 1H, J=9.00, 6.22), 2.10 (s, 3H), 1.27 (d, 3H, J=6.24); ¹³C NMR (62.9 MHz, CDCl₃) δ 170.4, 135.5, 131.3, 128.9, 128.5, 128.1, 127.3, 83.6, 70.7, 65.5, 21.0, 18.0; HRMS (E1): calcd for C₁₄H₁₆O₃S: 264.0821. Found: 264.0824.

EXAMPLE 9

3-O-Acetyl-1,5-anhydro-2-deoxy-L-ribo-hex-1-enopyranose (Compound 17).

Compound 13 (40.2 mg) was dissolved in CH₂Cl₂ (3.0 mL) and the resulting solution was cooled to zero degrees C. to form a reaction mixture. Solid MCPBA (36.8 mg) was added and the mixture was stirred for 30 minutes at zero degrees C. The reaction mixture was diluted with 20 mL CH₂Cl₂ and washed with 2×10 mL saturated NaHCO₃. The organics were dried over MgSO₄, filtered, and concentrated under reduced pressure. The residue was taken up in THF (2.0 mL), piperidine (75 μL) was added, and the resulting solution stirred for one hour at room temperature. The mixture was added to 10 mL H₂O and extracted with 2×5 mL CH₂Cl₂. The organics were dried over MgSO₄, filtered, and concentrated under reduced pressure. The residue was chromatographed on silica gel, eluting with hexane/EtOAc 8:2 to 6:4, to give 16.5 mg of Compound 17.

[α]D²⁵ −280.4° (CHCl₃, c 1.285); IR (CHCl₃) 3560, 3010, 1730, 1640, 1320, 1240, 1030, cm⁻¹; ¹H NMR (250 MHz, CDCl₃) δ 6.47, (d, 1H, J=5.93); 5.19 (t, 1H, J=4.79), 4.90 (t, 1H, 5.73), 3.94 (dq, 1H, J=10.05, 6.27), 3.70 (m, 1H), 2.11 (s, 3H), 1.39 (d, 3H, J=6.27); ¹³C NMR (62.9 MHz, CDCl₃) δ 171.4, 148.2, 97.1, 71.4, 70.7, 66.2, 21.2, 17.2; HRMS (CI): M+H calcd for C₈H₁₃O₄: 173.0814. Found 173.0816.

The foregoing is intended as illustrative of the present invention but not limiting. Numerous variations and modifications may be effected without departing from the true spirit and scope of the invention.

We claim:

1. A compound represented by the chemical formula

R² is selected from the group consisting of H, C₁-C₆ alkyl, 2-furyl, OR⁴, NR⁵R⁶ and SR⁶;

R³ is selected from the group consisting of H, C₁-C₆ alkyl, (CH₂)ₘOR⁴, 2-furyl, OR⁴, NR⁵R⁶, SR⁶, or R³ and R² form a cyclic acetal or ketal prepared from an aldehyde or ketone containing 1 to 12 carbon atoms;

m is zero, 1, 2, 3 or 4 (1-4) with the proviso that the number of carbon atoms in the glycal chain is not greater than 9, such that when m is zero, R³ is OR⁴, whereas when m is 1–4, m represents the number of methylene groups present;

n is zero or 1 such that when n is zero R²CH is absent, and when n is 1 R²CH is present;

R⁴ is selected from the group consisting of hydrogen, C₁-C₁₈ alkyl, C₆-C₁₀ aryl, C₁-C₁₈ acyl, C₇-C₁₀ aralkyl, tri-C₁-C₆ alkylsilyl, diaryl-C₁-C₆ alkylsilyl, aryldi-C₁-C₆ alkylsilyl, alkylsilyl diaryl C₁-C₆, and a substituted mono- or oligosaccharide;

R⁵ is selected from the group consisting of C₁-C₁₈ alkyl, C₆-C₁₀ aryl, C₇-C₁₀ aralkyl, tri-C₁-C₆ alkylsilyl, aryl di-C₁-C₆ alkylsilyl, diaryl C₁-C₆ alkylsilyl, and C₁-C₁₈ acyl;

R⁶ is selected from the group consisting of H, C₁-C₁₈ a alkyl, C₇-C₁₀ aralkyl, and C₁-C₁₈ acyl with the proviso that (a) at least one of R⁵ or R⁶ of NR⁵R⁶ and SR⁶ is C₁-C₁₈ acyl, or (b) NR⁴R⁵ together form a cyclic amide or imide containing five to seven atoms in the ring and a total of 4–10 carbon atoms;

R⁷ and R⁸ are independently H or C₁-C₉ alkyl with the proviso that the number of carbon atoms in R⁷ plus those of R⁸ is nine or fewer; and R⁹ is selected from the group consisting of hydrogen (H), or C₁-C₆ alkyl, CO₂R⁴, CN, CH₂OR⁴, 2-furyl,

R[10] is selected from the group consisting of hydrogen (H) 2-furyl, or $C_1$-$C_6$ alkyl; and R[11] is an organic radical having fewer than 15 carbon atoms.

2. The compound according to claim 1 wherein n is 1, and R[9] and R[10] are both hydrogen.

3. The compound according to claim 2 wherein R[11] is selected from the group consisting of phenyl, substituted phenyl and $C_1$-$C_6$ lower alkyl.

4. A compound of the formula

5. A compound of the formula

6. A compound of the formula

* * * * *